(12) United States Patent
Renard

(10) Patent No.: US 7,357,505 B2
(45) Date of Patent: Apr. 15, 2008

(54) DEVICE FOR SELF-MEASUREMENT OF INTERPUPILLARY DISTANCE

(76) Inventor: Paula A. Renard, P.O. Box 841, Los Alamos, CA (US) 93440

( * ) Notice: Subject to any disclaimer, the term of this patent is extended or adjusted under 35 U.S.C. 154(b) by 377 days.

(21) Appl. No.: 11/099,385

(22) Filed: Apr. 4, 2005

(65) Prior Publication Data
US 2006/0238705 A1    Oct. 26, 2006

(51) Int. Cl.
A61B 3/10    (2006.01)
(52) U.S. Cl. ..................................... 351/204
(58) Field of Classification Search .............. 351/204, 351/223, 245
See application file for complete search history.

(56) References Cited

U.S. PATENT DOCUMENTS 5,461,434 A * 10/1995 Blattberg .................. 351/204
5,757,460 A * 5/1998 Cockley .................... 351/205
5,822,032 A * 10/1998 Edwards et al. ........... 351/204

* cited by examiner

Primary Examiner—Alicia M Harrington

(57) ABSTRACT

A device for self-determining a person's pupillary separation in an OTC setting. In a first embodiment, the device includes a plurality of interconnected masks, each mask having two holes therein, the distance between the center of the holes being indicated on the mask. The separation of the holes is different for each mask. The user places the respective masks before the eyes and looks through the holes. The optimal interpupillary distance is determined by the clearest vision experienced by the user when looking through the holes. In a second embodiment, a single mask is presented wherein the distance between two holes is varied continuously until a single hole is perceived by the user, and the interpupillary distance read from a ruled scale on the device.

12 Claims, 2 Drawing Sheets

DEVICE FOR SELF-MEASUREMENT OF INTERPUPILLARY DISTANCE

BACKGROUND OF THE INVENTION

1. Field of the Invention

The present invention relates to devices for the self-determination of a person's interpupillary distance.

2. Prior Art

OTC reading glasses have been available for many years. Most have been single vision half-eye designs to enable the wearer to look over the top for distance use, and also different straight top bifocal designs to allow the wearer to view distant images through a plano (zero power) segment without the need for removing the glasses. The problem with current over-the-counter (OTC) reading glasses is that they are not made with customized pupillary distance (PD's) as is done in custom-made spectacles. The PD of prior art bifocal glasses, as currently manufactured, depends on the geometric or mechanical center of the frame itself, wherein the optical center of the lens is centered in the geometric center of the frame. Large frames have large distances between the optical centers of the lenses. A person with a narrow pupillary distance (PD) measurement of, for example, 56 mm., could be wearing OTC reading glasses with 66 mm. optical centers. This creates up to 2 diopters of induced prism effect that would cause eyestrain and discomfort and would be outside of ANSI standards for ophthalmic lenses.

As the age of the population increases, many people with otherwise healthy eyes are becoming presbyopic: a loss of the eyes' ability to see objects close up such as small print and reading materials. Presbyopes currently must get an eye exam in order to acquire glasses having the correct PD because a choice of spectacles having different PD's have not been available OTC, and need to be custom made.

The need for a simple device that can be used to self-determine the PD has been recognized and addressed in the art. For example, Blattberg, in U.S. Pat. No. 5,461,434, discloses a method and apparatus for interpupillary distance measurement. The device includes a frame and a pair of sliders. In use, the sliders are mounted in the frame and adjusted horizontally apart by the user and fixed in that position for later measurement. A bifocal or multifocal optical centering device and method is also described. The optical centering device includes a frame which is attached to a spectacle lens and a slider adjusted therein relative to the user's eye. The position of the slider is then fixed for later measurement.

Edwards et al., in U.S. Pat. No. 5,822,032, discloses a device for measuring the interpupillary distance of the eyes. The device has a frame having a first hole which is positionable at the pupil of the person's left eye, and a disk rotatably mounted on the frame which is rotatable about an axis perpendicular to the face of the frame. The disk has a plurality of second holes which spiral radially outwardly on the disk from the axis. By rotating the disk, one of the second holes is viewable through a window in the frame and positionable at the pupil of the person's right eye. The interpupillary distance (PD) is equal or approximately equal to the distance between the centers of the first and second holes when the holes are positioned at the respective pupils of the person. Numerals representing the PD appear on the surface of the disk through another window in the frame.

While OTC spectacles are currently available in a variety of powers, there is a need for OTC spectacles that are also available in a plurality of PD's for each power. While it is optimal but impractical to provide OTC glasses in all possible PD's, it is both sensible and practical to provide OTC glasses in several PD's (such as, for example, SMALL, MEDIUM and LARGE) for each power so that after a person selects the correct power, the user can further select the glasses having a PD that best fits their interpupillary separation. In the event that such OTC glasses become available in the future, there will be a need for a device that enables a person to easily determine his/her personal PD, in an OTC setting, in order to select OTC spectacles having not only the correct power, but also having a PD that most closely approximates their personal PD.

SUMMARY

In accordance with one aspect of the present invention, a device operable for permitting a user to self-determine his/her approximate personal interpupillary distance (PD). If the PD of OTC reading glasses are determined at the factory, and the PD indicated on the glasses, the user may then use the self-determined personal PD to identify OTC glasses having both the correct power and the correct PD.

The features of the invention believed to be novel are set forth with particularity in the appended claims. However the invention itself, both as to organization and method of operation, together with further objects and advantages thereof may be best understood by reference to the following description taken in conjunction with the accompanying drawings.

DESCRIPTION OF THE PREFERRED EMBODIMENTS

Figure 1:
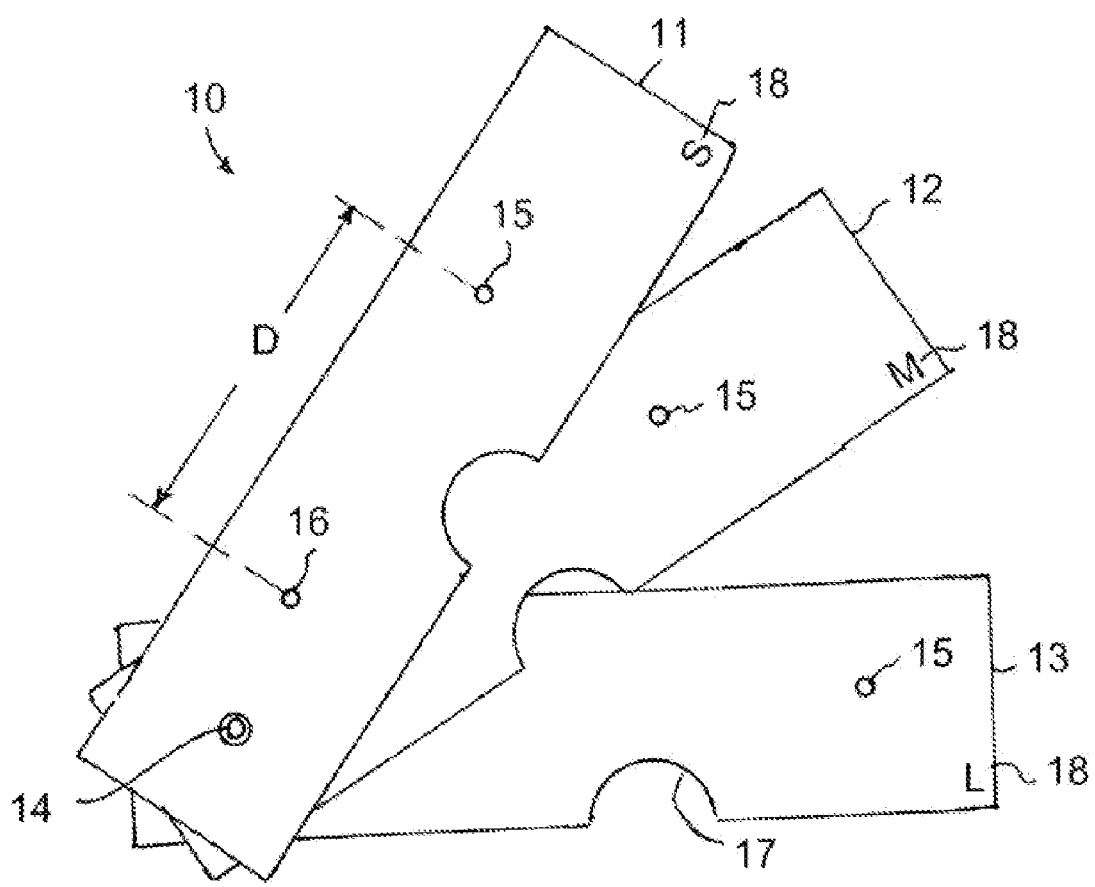
FIG. 1 is a perspective view of a PD device in accordance with a first embodiment of the present invention comprising a plurality of interconnected, biapertured masks, the spacing between the holes in the masks being different for each mask.

With reference now to FIG. 1, a first embodiment of a device operable for measuring the approximate interpupillary distance (PD) of a user's eyes is generally indicated at numeral 10. The device 10 comprises at least three masks 11-13 interconnected to one another at an end thereof by pivotal attachment means 14 such as a rivet. The rivet may also provide means for attaching the device 10 to a fixture such as a display stand. Each mask has a right hole 15 and a left hole 16 therein (the left hole 16 is not visible in masks 12 and 13), spaced by a distance D wherein D is different for each of the masks 11-13. Each mask preferably further includes a semicircular notch 17 in a lower edge thereof centered between holes 15 and 16 adapted to partially encircle the bridge of a user's nose. When a user wishes to determine his/her PD, the masks are serially placed before the eyes with the bridge of the nose disposed within the notch 17 and the user looks through the holes 15 and 16 with respective right and left eyes. If the (preferably circular) holes 15 and 16 in any mask 11-13 are spaced such that the distance D is equal to the interpupillary spacing (PD) of the user, greatest visual acuity will be experienced by the wearer indicating the correct lens spacing for the particular user. For example, a single hole will be perceived by the user when the mask has the correct PD. Accordingly, each of the masks 11, 12 and 13 bears a mark 18 indicating the PD for the particular mask. If OTC spectacles are presented having a selection of PD's for each power such as, for example, small (S), medium (M) and large (L), the spectacles having the correct power and the closest PD can be selected by the user.

Figure 2:
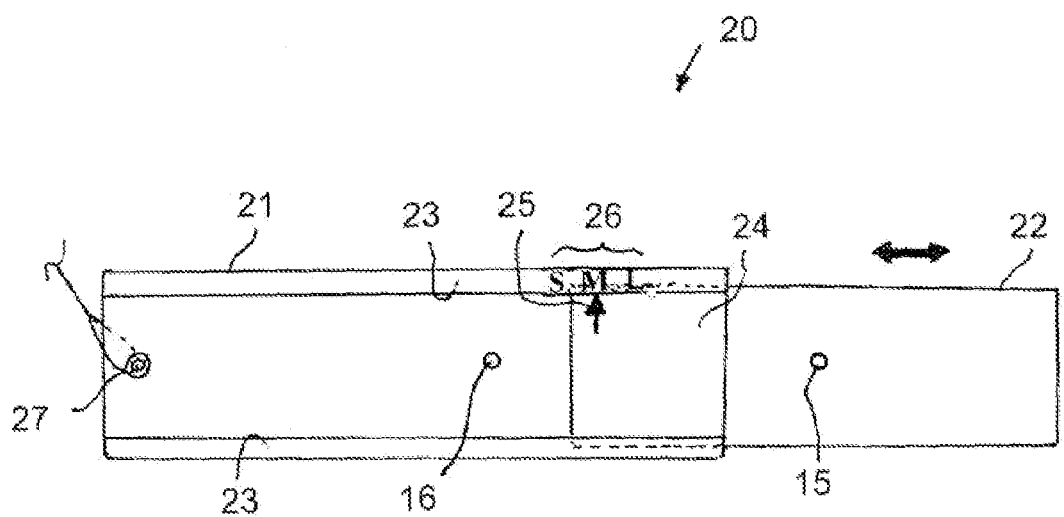
FIG. 2 is a plan view of a slidingly adjustable PD device in accordance with a second embodiment of the present invention.

A second embodiment of a device operable for the self-determination of PD by a user is indicated at numeral 20 in FIG. 2. The device 20 comprises a grooved apertured member 21 and an apertured sliding member 22. Grooved member 21 has a hole 16 therein and a pair of parallel grooves 23 on the outer edges thereof. The grooves 23 are dimensioned to slidingly receive an end portion 24 of the sliding member 22 therewithin. When the sliding member 22 is slid reciprocally within the grooves 23 in the direction of the double-ended arrow, the distance between the holes 15 and 16 varies. When a user places the device before the face such that the left hole 16 is in front of his/her left pupil, if the sliding member is moved until the spacing between the holes 15 and 16 is equal to the PD of the user, the user will perceive a single hole. The sliding member 22 has a marker 25 thereon, and the grooved member 21 has a PD indicator scale 26 disposed adjacent the marker 25. When the distance between the holes 15 and 16 is equal to the user's PD, the holes 15 and 16 will be perceived as a single hole by the user. The user's PD can then be read from the PD scale 26 adjacent the mark 25. The device 20 preferably includes attachment means 27 operable for attaching the device 20 to a relatively permanent fixture such as a spectacle display stand to prevent loss of the device.

In the examples of the first and second embodiments of the PD device shown in FIGS. 1 and 2, the PD is indicated to be "small", medium" or "large"; each of which are relative terms. The choice of PD indicator on the PD scale 26 is more or less arbitrary, but is related, preferably linearly, to the interpupillary distance. Since the average PD for an adult is about 60 mm, the range of the PD scale 26 should be sufficient to indicate a PD between about 55 mm (S) and 65 mm (L). Both embodiments of the devices 10 and 20 are easy to use for self-determining a user's PD in an OTC setting, and relatively inexpensive to manufacture from common opaque materials such as cardboard or plastic.

While particular embodiments of the present invention have been illustrated and described, it would be obvious to those skilled in the art that various other changes and modifications can be made without departing from the spirit and scope of the invention. For example, the device 10 or 20 can be used to determine the correct interpupillary distance for a particular user with single focus, bifocal, trifocal or continuous focal length glasses. Further, it is contemplated that in the future, not only OTC glasses be available in a plurality of PD's, but that OTC glasses having means thereon operable for adjusting the PD of the glasses will be available. The devices 10 or 20 can be used as a guide for adjusting the PD of such OTC spectacles to match his/her personal PD. It is therefore intended to cover in the appended claims all such changes and modifications that are within the scope of this invention.

What I claim is:

1. A device operable for enabling a user to self-determine his/her approximate interpupillary distance comprising a plurality of at least three elongate, interconnected masks, each mask having two holes therein separated by a distance, said distance being indicated on the mask by a mark indicating said interpupillary distance for said mask, and wherein said distance is different for each mask.

2. The device of claim 1 wherein one mask has a distance of about 55-58 millimeters, and another mask has a distance of about 63-66 millimeters.

3. The device of claim 2 wherein a third mask has a distance of about 60 millimeters.

4. The device of claim 1 wherein said plurality of masks are interconnected to one another by pivotal attachment means.

5. The device of claim 4 wherein said pivotal attachment means is a rivet.

6. The device of claim 1 wherein said plurality of masks each have an attachment hole in an end thereof and wherein said plurality of masks are interconnected by a ring passing through said attachment holes.

7. A device operable for enabling a user to self-determine his/her approximate interpupillary distance comprising an opaque, substantially flat, elongate first sheet having a first hole therein and a pair of grooves on opposing edges thereof, and an opaque, substantially flat, elongate second sheet having a second hole therein slidably mounted in said grooves such that when said second sheet is slid in said grooves, a distance between said first and second holes changes.

8. The device of claim 7 wherein said first sheet or said second sheet has indicia thereon that provides a measure of said distance between said first and second holes.

9. The device of claim 8 further comprising attachment means operable for attaching said device to a fixture.

10. The device of claim 9 wherein said attachment means is a lanyard.

11. The device of claim 7 further comprising attachment means operable for attaching said device to a fixture.

12. The device of claim 11 wherein said attachment means is a lanyard.

* * * * *